US011033271B2

(12) United States Patent
Smith et al.

(10) Patent No.: US 11,033,271 B2
(45) Date of Patent: Jun. 15, 2021

(54) REMOVABLE ANASTOMOSIS SUTURING SUPPORT

(71) Applicant: Spiration, Inc., Redmond, WA (US)

(72) Inventors: Adam Lee Smith, Palm Desert, CA (US); Clifton A. Alferness, Olalla, WA (US); Gina M. Muia-Longman, Seattle, WA (US); Clinton L. Finger, Bellevue, WA (US); David R. Seward, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 175 days.

(21) Appl. No.: 16/367,164

(22) Filed: Mar. 27, 2019

(65) Prior Publication Data

US 2020/0305875 A1 Oct. 1, 2020

(51) Int. Cl.
*A61B 17/11* (2006.01)
*A61B 17/04* (2006.01)
*A61B 17/06* (2006.01)

(52) U.S. Cl.
CPC .......... *A61B 17/11* (2013.01); *A61B 17/0469* (2013.01); *A61B 17/0482* (2013.01); *A61B 17/06066* (2013.01); *A61B 2017/1107* (2013.01); *A61B 2017/1135* (2013.01)

(58) Field of Classification Search
CPC ............ A61B 17/11; A61B 2017/1135; A61B 2017/1107; A61B 17/1114; A61B 2017/1139; A61B 17/115; A61B 2017/1132; A61B 2017/1103; A61B 17/0469; A61F 2/064
See application file for complete search history.

(56) References Cited

U.S. PATENT DOCUMENTS

| 6,514,263 | B1 | 2/2003 | Stefanchik et al. |
| 6,530,932 | B1 | 3/2003 | Swayze et al. |
| 6,613,058 | B1 | 9/2003 | Goldin |
| 2013/0006281 | A1* | 1/2013 | Golden .............. A61B 17/0057 606/153 |

OTHER PUBLICATIONS

Assessment of Patented Coronary End-to-Side Anastomotic Devices Using Micromechanical Bonding Ann Thorac Sorg, 2000.

* cited by examiner

*Primary Examiner* — Katherine M Shi
(74) *Attorney, Agent, or Firm* — Clements Bernard Walker; Frank J. Bozzo (57) ABSTRACT

Disclosed embodiments include apparatuses, systems, and methods for facilitating surgical anastomosis. In an illustrative embodiment, an apparatus includes a first connector configured to engage an opening of a donor passage. A second connector is configured to engage an opening in a receiving passage. A separator is configured to support the first connector and the second connector and to fix relative positions of the end of the donor passage to edges of the opening in a receiving passage across a gap. The separator is configured to maintain the gap between the first connector and the second connector while multiple loops of a suture are passed through the edge of the opening in the donor passage and the edges of the opening in the receiving passage. The first connector, the second connector, and the separator are further configured to be removed from between adjacent loops of the multiple loops of the suture.

17 Claims, 10 Drawing Sheets

REMOVABLE ANASTOMOSIS SUTURING SUPPORT

FIELD

The present disclosure relates to apparatuses, systems, and methods for presenting and joining an opening of a donor passage to an opening in a receiving passage.

BACKGROUND

The statements in this section merely provide background information related to the present disclosure and may not constitute prior art.

Surgical anastomosis enables segments of one or more arteries, blood vessels, intestines, or any other passages to be connected or reconnected, such as in coronary artery bypass graft (CABG) procedures. In a CABG procedure, for example, a saphenous vein may be harvested from a patient's leg and grafted to circumvent a coronary arterial blockage. Such procedures are tremendously useful and may regularly save and extend lives.

However, CABG procedures and similar procedures involve highly invasive surgery. For example, a typical CABG procedure involves performing a median sternotomy in which a vertical incision is made along the patient's sternum, after which the sternum itself is actually broken open to provide access to the heart and surrounding arteries. The median sternotomy provides a surgeon with space to insert a graft and suture the graft to a coronary artery to complete the process. However, the sizable incision and the breaking of the sternum may involve significant scarring, discomfort, and risk of infection, and may require significant recovery time for the healing of the affected structures.

SUMMARY

Disclosed embodiments include apparatuses, systems, and methods for facilitating surgical anastomosis between bodily passages, such as veins, arteries or other passages.

In an illustrative embodiment, an apparatus includes a first connector configured to engage an opening of a donor passage. A second connector is configured to engage an opening in a receiving passage. A separator is configured to support the first connector and the second connector, and is further configured to fix relative positions of the opening of the donor passage to edges of the opening in the receiving passage across a gap. The separator is configured to maintain the gap between the first connector and the second connector with multiple loops of a suture being passed through the edges of the opening in the donor passage and the edges of the opening in the receiving passage across the gap. The first connector, the second connector, and the separator are further configured to be removed from between adjacent loops of the multiple loops of the suture.

In another illustrative embodiment, a system includes a needle configured to draw a suture through an edge of the opening of a donor passage and edges of an opening in a receiving passage. A first connector is configured to engage the opening of a donor passage. A second connector is configured to engage an opening in a receiving passage. A separator is configured to support the first connector and the second connector and further configured to fix relative positions the edges of the opening of the donor passage to edges of the opening in a receiving passage across a gap. The separator is configured to maintain the gap between the first connector and the second connector with multiple loops of a suture being passed through the edges of the donor passage and the edges of the opening in the receiving passage across the gap. The separator is further configured to be removed from between adjacent loops of the multiple loops of the suture.

In a further illustrative embodiment, a method includes fixing relative positions of an opening of a donor passage to edges of an opening in a receiving passage across a gap with a temporary coupling extending from inside the end of the donor passage to inside the receiving passage. Multiple loops of a suture are alternately passed through the edges of the opening of the donor passage and the edges of the opening in the receiving passage across the gap. A part is formed between adjacent loops of the multiple loops of the suture. The temporary coupling is removed from the inside of the opening of the donor passage and the inside of the receiving passage. The temporary coupling is withdrawn through the part between the adjacent loops. The suture is drawn tight to close the gap between the edges of the opening of the donor passage and the edges of the opening in the receiving passage to suture the opening of the donor passage to the opening in the receiving passage.

Further features, advantages, and areas of applicability will become apparent from the description provided herein. It will be appreciated that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

It will be noted that the first digit of three-digit reference numbers and the first two digits of four-digit reference numbers correspond to the first digit of one-digit figure numbers and the first two digits of two-digit figure numbers, respectively, in which the element first appears.

The following description explains, by way of illustration only and not of limitation, various embodiments of noninvasive apparatuses, systems, and methods for positioning a donor passage relative to a receiving passage, and for suturing the passages together in a surgical anastomosis procedure. The apparatuses, systems, and methods are described using the example of a CABG procedure involving the joining of a saphenous vein to a coronary artery in a CABG procedure. However, it will be appreciated that the same methods, apparatuses, and systems may be used for other grafting or anastomosis procedures for other arteries, intestines, or other bodily passages.

Figure 1:
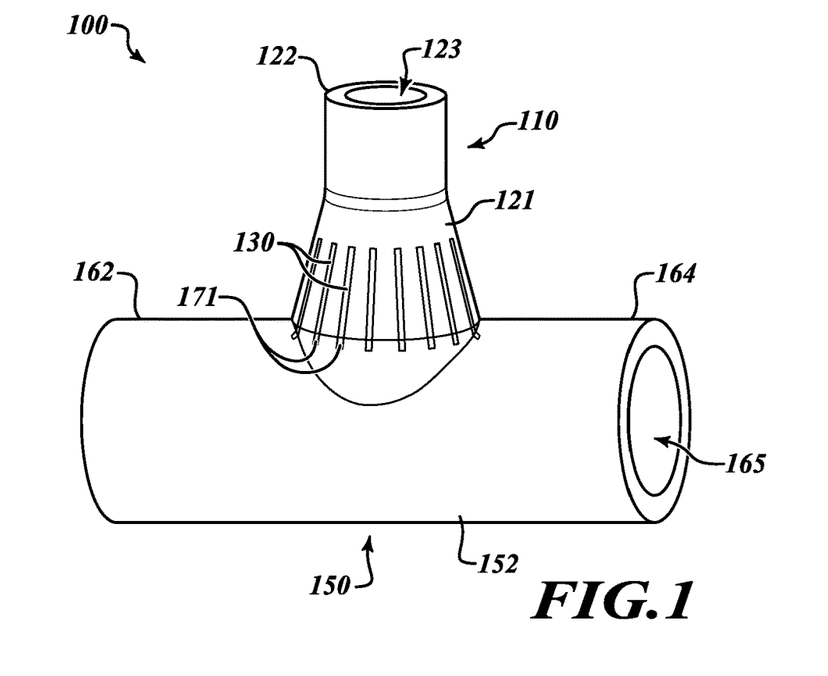
FIG. 1 is a perspective view of an embodiment of an apparatus for temporarily securing passages to be joined in an anastomosis procedure.

Referring to FIG. 1, in various embodiments an apparatus 100 for facilitating surgical anastomosis of bodily passages includes a first connector 110 and a second connector 150. The first connector 110 is configured to engage a donor passage (not shown in FIG. 1). An end 122 of the first connector 110 includes a first port 123 configured to receive a flow of fluid from the donor passage. The second connector 150 is configured to engage a receiving passage (not shown in FIG. 1), with a body 152 of the second connector 150 being received into the receiving passage. A first end 162 and a second end 164 of the body 152 of the second connector 150 include ports, such as a second port 165 in the second end 164, to facilitate a flow of fluid through the second connector 150 into the receiving passage, as further described below.

With the end 122 of the first connector 110 engaging the donor passage and the body 152 of the second connector 150 received into the receiving passage, in various embodiments a separator 121 between the first connector 110 and the second connector 150 supports the donor passage and the receiving passage across a gap across which sutures will be formed. With the donor passage and the receiving passage supported in place, channels 130 and 171 in the surface of the first connector 110 and the body 152 of the second connector 152, respectively, help to direct a needle (not shown in FIG. 1) to form sutures to join the donor passage and the receiving passage.

Figure 2:
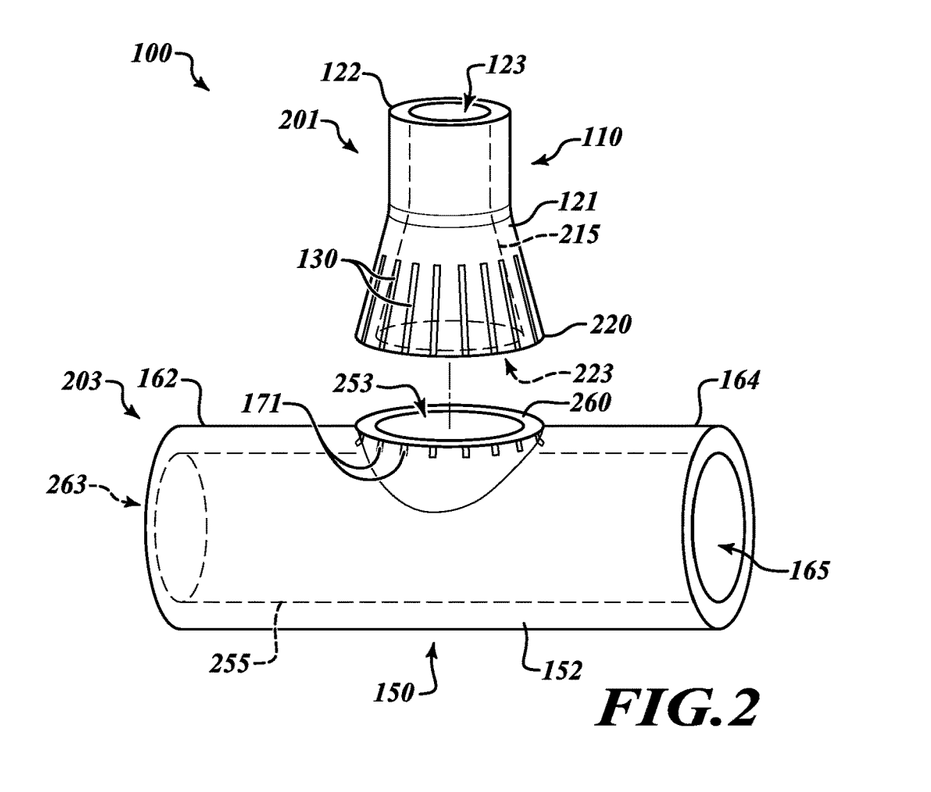
FIG. 2 is a perspective view in partial cutaway form of an embodiment of the apparatus of FIG. 1 that includes separate coupling segments for temporarily securing the passages.

Referring to FIG. 2, in other embodiments an apparatus 200 includes separate segments including a first coupling segment 201 and a second coupling segment 203. In an illustrative embodiment, the first coupling segment 201 includes the first connector 110 and the separator 121, while the second coupling segment 203 includes the second connector 150. Presenting two separate coupling segments 201 and 203 may simplify the process of inserting the connectors 110 and 150 into the passages (not shown in FIG. 2) and the process of removing the connectors 110 and 150 from the passages, as further described below.

In various embodiments a base end 220 of the first coupling segment 201 is configured to engage a base end 260 of the second coupling segment 203. A base port 223 in the first coupling segment 201 is configured to engage a base port 253 in the second coupling segment 203 to fluidly connect a donor channel 215 in the first coupling segment 201 with a receiving channel 255 in the second coupling segment 203. The receiving channel 255 fluidly couples a first port 263 in the first end 162 with the second port 165 in the second end 164 of the second connector 150. The receiving channel 255 also may be fluidly coupled with the donor channel 215 when coupled therewith, as further described below. The base ends 220 and 260 may be joined magnetically or mechanically to hold them in place to maintain the gap between the passages. The base ports 223 and 253 may include one or more gaskets or seals (not shown in FIG. 2) to enhance the fluid connection between the donor channel 215 and the receiving channel. One or both of the base ports 223 and 253 also may include a seal that is configured to open when the base ends 220 and 260 are joined together. Thus, the base port 223 may close the donor channel 215 and the base port 253 may close the receiving channel 255 until the base ports 223 and 253 are connected. For one example, the base ports 223 and 253 may include flaps that are forced open when the base ports 223 and 253 are connected.

Figure 3A:
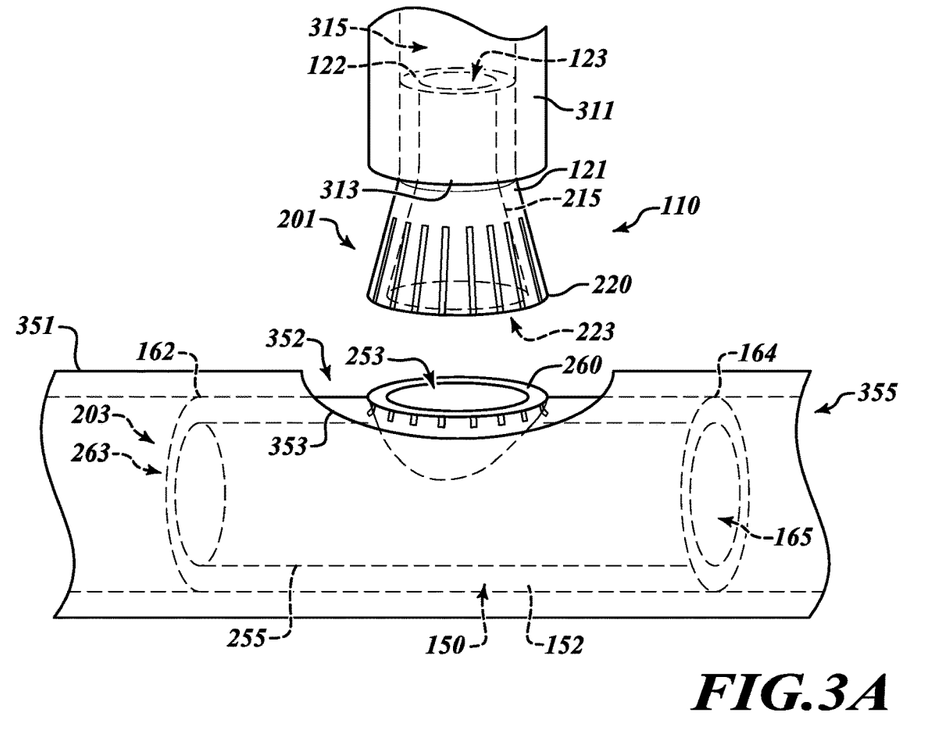
FIGS. 3A and 3B are schematic diagrams in partial cutaway form of the apparatus of FIG. 2 being inserted to temporarily secure the passages.

Referring to FIG. 3A, in various embodiments the first connector 110 and the second connector 150 are positioned to support an anastomosis procedure. The end 122 of the first connector 110 is inserted into an end 313 of the donor passage 311. The body 152 of the second connector 150 is inserted into an opening 352 in the receiving passage 351. FIG. 3A depicts the apparatus 200 of FIG. 2 in which the connectors 110 and 150 are included in different connector segments 201 and 203. However, it will be appreciated that the insertion of the connectors 110 and 150 into the passages 311 and 351, respectively, could be performed using the apparatus 100 of FIG. 1 in which the connectors 110 and 150 are not part of different segments.

As previously stated, the end 122 of the first connector 110 is inserted into the end 313 of a donor passage 311. In the example of a CABG procedure, the donor passage 311 may include a saphenous vein harvested from a patient's leg. The end 122 of the first connector 110 is thereby fluidly coupled with an interior 315 of the donor passage 311. The body 152 of the second connector 150 is inserted into the opening 352 in the receiving passage 351 and situated within an interior 355 of the receiving passage 351. The opening 352 may be formed by making an incision in the receiving passage 351 with a scalpel, an endoscopic scalpel, or another cutting apparatus. The second connector 150 should be positioned within the opening 352 in receiving passage 351 so that the base end 250 is accessible to the base end 220 of the first connector 110 between edges 353 of the opening 352.

Figure 3B:
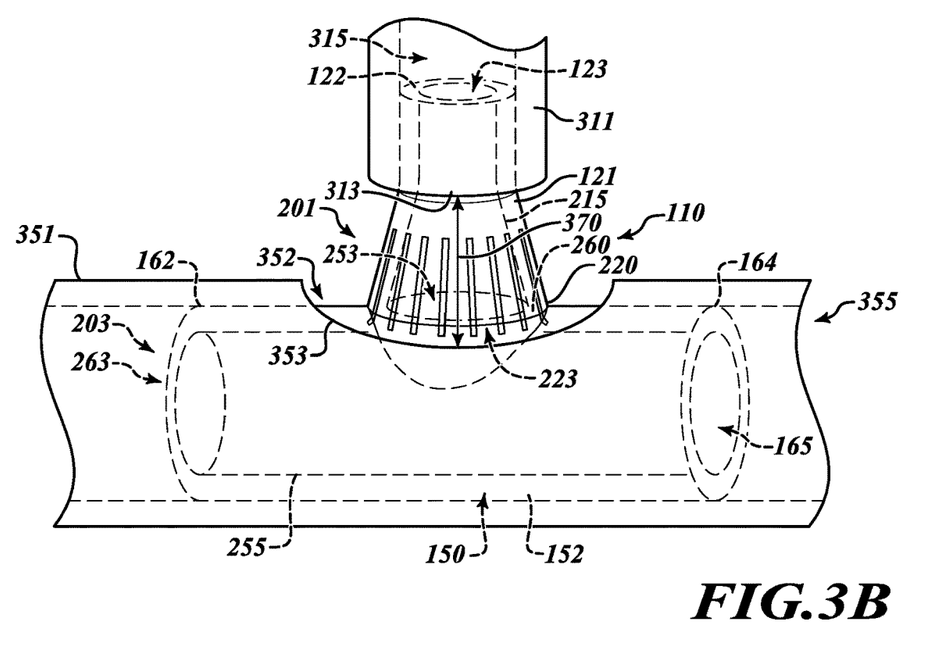

Referring to FIG. 3B, in various embodiments the base end 220 of the first connector 110 is moved to engage the base end 260 of the second connector 150. Coupling the base ends 220 and 260 thus joins together the first coupling segment 201 and the second coupling segment 203 of the apparatus 200 of FIG. 2. As previously described, the base ends 220 and 260 may be joined magnetically or mechanically to hold them in place to form and maintain a gap 370 between the end 313 of the donor passage 311 and the opening 352 formed in the receiving passage 351. Magnets in surfaces of one or more of the base ends 220 and 260 may hold the base ends 220 and 260 together until mechanically forced apart. As also previously mentioned, the base ports 223 and 253 (not shown in FIG. 3B) in the base ends 220 and 260, respectively, may include one or more gaskets to frictionally engage one another to hold the base ends 220 and 260 together until mechanically forced apart. Joining together the base ends 220 and 260 fluidly couples the base port 223 in the base end 220 of the first connector 110 with the base port 253 in the base end 260 of the second connector 150. Seals (not shown) included in one or both of the base ports 223 and 253 may be forced open by the engagement of the base ports 223 and 253.

Figure 4:
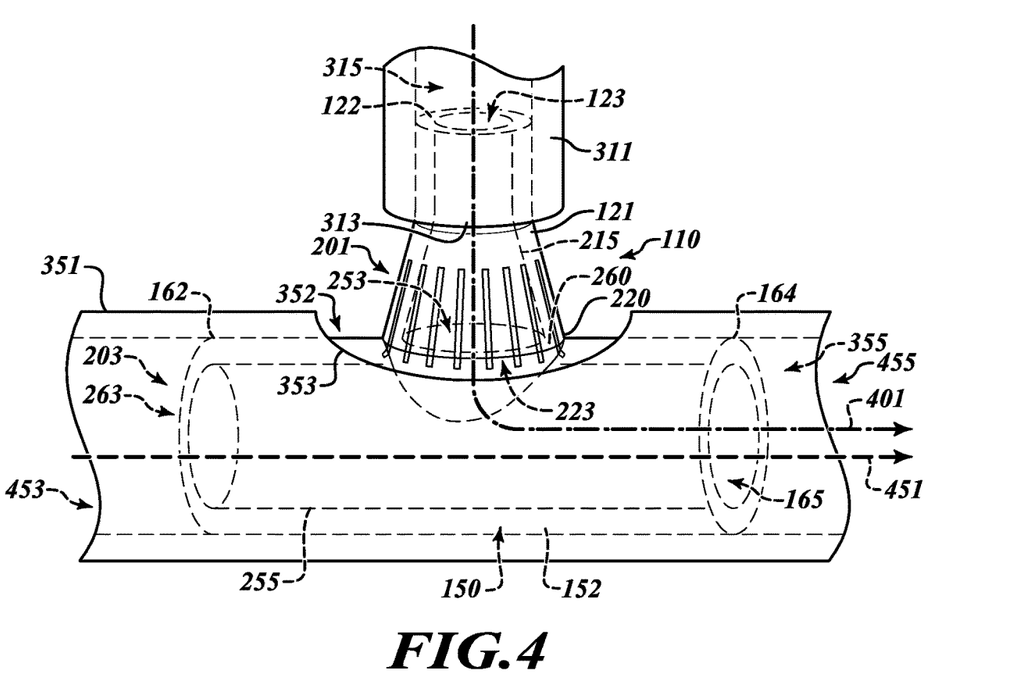
FIG. 4 is a schematic diagram in partial cutaway form of the apparatus of FIG. 2 showing the flow of fluids from the passages through the apparatus.

Referring to FIG. 4, in various embodiments the coupling of the base ports 223 and 253 fluidly couples the donor channel 21 in the first connector 110 with the receiving channel 255 in the second connector 150. Thus, with the base ends 220 and 260 engaged, a donor fluid flow 401 (represented by a dashed line) flowing in the interior 315 of the donor passage 311, such as a supply of blood, may flow via the donor channel 215 into the receiving channel 255 and into the interior 355 of the receiving passage 351. At the same time, an original fluid flow 451 (represented by a dotted and dashed line) may continue to flow via the receiving channel 255 from a first longitudinal side 453 of the receiving passage 351 at the first end 162 of the second connector 150 to a second longitudinal side 455 of the receiving passage 351 at the second end 164 of the second connector 150. As a result, the donor fluid flow 401 from the interior 31 of the donor passage 311 and/or the original fluid flow 451 may continue to flow through to the second longitudinal side 455 of the receiving passage 351 as the end 313 of the donor passage 311 is sutured to the edges 353 of the opening 352 in the receiving channel 351, as further described below.

Figure 5A:
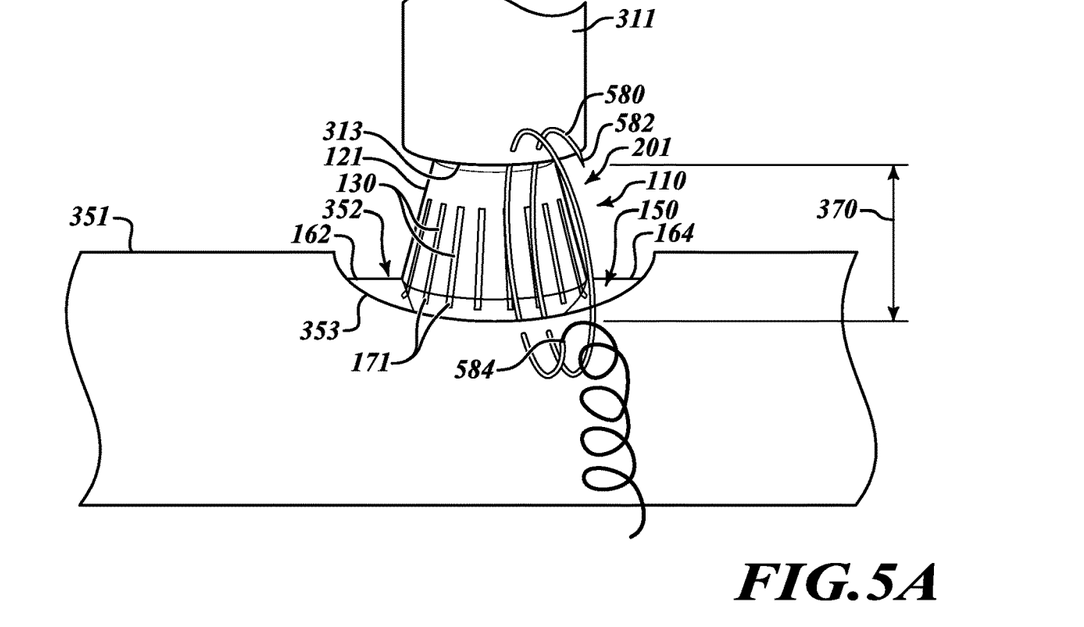
FIGS. 5A and 5B are schematic diagrams of the apparatus of FIG. 2 temporarily securing the passages while the passages are sutured together.

Referring to FIG. 5A, with the connectors 110 and 150 in place, in various embodiments suturing of the end 313 of the donor passage 311 to the edges 353 of the opening 352 formed in the receiving passage 351 is initiated. As previously described, the connectors 110 and 150 maintain a gap 370 between the end 313 of the donor passage 311 and the edges 353 of the opening 352 formed in the receiving passage 351. The gap 370 is maintained while the sutures are put in place and thereby provides an opening through which the connectors 110 and 150 may be withdrawn from the donor passage 311 and the receiving passage 351, as further described below.

Suturing is performed with a needle 580. In various embodiments the needle 580, as described further below with reference to FIGS. 6A and 6B, includes a first pointed end 582. The first pointed end 582 is configured to pierce tissue, such as the tissue comprising the donor passage 311 and the receiving passage 351. The needle 580 also includes a trailing end 584 configured to be joined with or to receive an end of a filament 590. The filament 590 may be used to suture together the end 313 of the donor passage 311 and the edges 353 of the opening 352 formed in the receiving passage 351. To facilitate the suturing, the needle 580 may be inserted through the tissue of the receiving passage 351 along the edges 353 of the opening 352. The needle may then be directed along the channels 171 and 130 on surfaces of the second connector 150 and the first connector 110, respectively. The needle 580 then may be directed outwardly through the tissue of the donor passage 311.

In various embodiments the channels 130 in the surface of the first connector 110 may be shaped to direct the needle 580 outwardly from the first connector 110 through the tissue of the donor passage 311. It will be appreciated that the suturing process also may be conducted in an opposite direction. The needle 580 may be inserted through the tissue of the donor passage 311 near the end 313, then directed along the channels 130 and 171 on surfaces of the first connector 110 and the second connector 150, respectively. The needle 580 may then be directed outwardly through the tissue of the receiving passage 351. The channels 171 in the surface of the second connector 150 may be shaped to help direct the needle 580 outwardly from the second connector 150 through the tissue of the receiving passage 351.

Figure 5B:
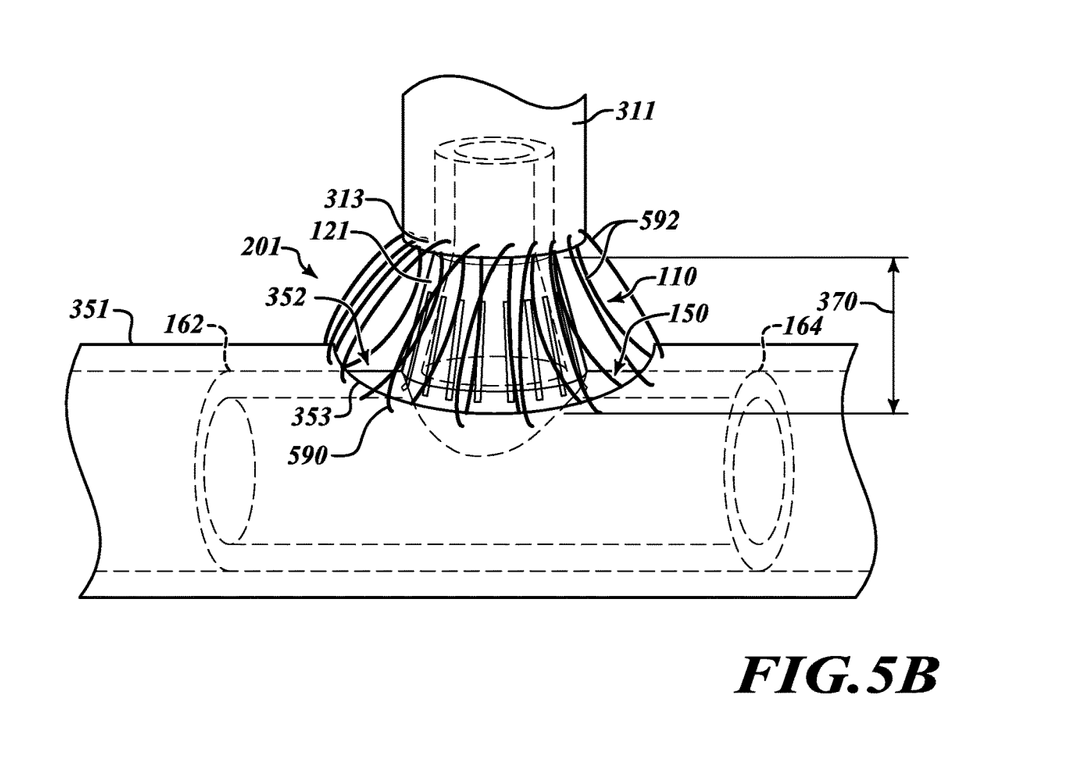

Referring to FIG. 5B, in various embodiments the suturing continues until multiple parachute stitches 592 extend fully around a periphery of the end 313 of the donor passage 311 and the opening 353 of the receiving passage 351. The suturing is performed with the gap 370 between the end 313 of the donor passage and the edges 353 of the opening 352 in the receiving passage 351, where the gap 370 is maintained by the separator 121 between the connectors 110 and 150. The parachute stitches 592 eventually will be drawn tight to complete the suturing of the end 313 of the donor passage 311 to the edges 353 of the opening 352 in the receiving passage 351, but not until the connectors 110 and 150 and the separator 121 are withdrawn from between the parachute stitches 592, as further described below.

Figure 6A:
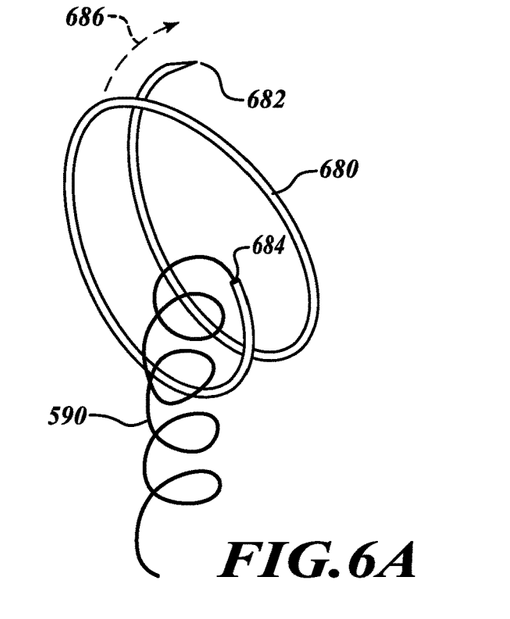
FIGS. 6A and 6B are schematic diagrams of alternative embodiments of needles that may be used to suture the passages.
Figure 6B:
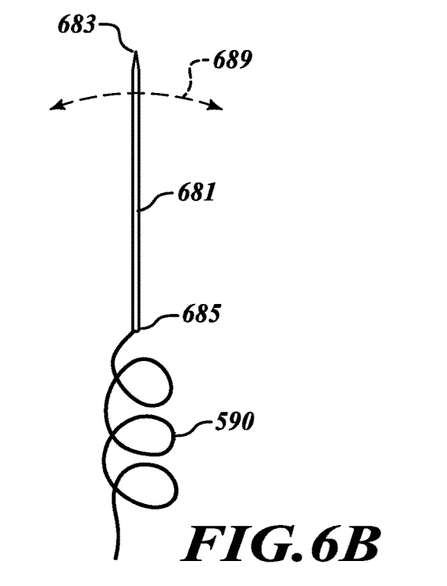

Referring to FIGS. 6A and 6B, in various embodiments different forms of needles may be used to perform the suturing as described with reference to FIGS. 5A and 5B. Referring to FIG. 6A, a rigid or semi-rigid needle 680 may be used to perform the suturing as described with reference to FIGS. 5A and 5B. The needle 680 may have a pointed end 682 adapted to pierce tissue. The needle 680 also may include a trailing end 684 configured to be joined with or to receive the end of the filament 590, as previously described with reference to the needle 580 (FIGS. 5A and 5B). The needle 680 may be formed in a helical shape having a radial curve 686. The helical shape of the needle 680 is configured to facilitate guiding the needle through the tissue of the receiving passage 351, through the channels 130 and 171 on the surfaces of the connectors 110 and 150, respectively, and back through the tissue of the donor passage 311. In various embodiments, the needle 680 extends radially through at least one complete circular transit so that, as a portion of the needle 680 passes near or along the apparatus 100 and through the end 313 of the donor passage 311 and/or the edges 353 of the opening 352 in the receiving passage 351, an opposite portion of the needle 680 may be engaged at an opposing side to motivate the needle 680 to continue the suturing procedure. The needle 680 may be sized to fit within the channels 130 and 171 on surfaces of the first connector 110 and the second connector 150, respectively.

Referring to FIG. 6B, in various embodiments a flexible needle 681 may be used to perform the suturing as described with reference to FIGS. 5A and 5B. The needle 681 may have a pointed end 683 adapted to pierce tissue. The needle 681 may also include a trailing end 685 configured to be joined with or to receive the end of the filament 590, as previously described with reference to the needle 580 (FIGS. 5A and 5B). The needle 681 may be sized to fit within the channels 130 and 171 on surfaces of the first connector 110 and the second connector 150, respectively. The needle 681 may have a generally straight shape, but be formed of a flexible material adapted to flex in directions 689 perpendicular to its axis. The flexibility of the needle 681 thus may allow the needle 681 to be directed into and follow the shape of the channels 130 and 171. As previously described, the channels 130 and 171 may be shaped to direct the needle 681 out of the channel and back through tissue of the passages 311 and 351.

Referring to FIGS. 7A through 8B, once the parachute stitches 592 are in place, in various embodiments the parachute stitches 592 may be parted to permit the withdrawal of the coupling segments 201 and 203. As previously described, the coupling segments 201 and 203 supported the relative positioning of the donor passage 311 and the receiving passage 351 while they were loosely sutured with the parachute stitches 592. However, with the parachute stitches 592 in place, the coupling segments 201 and 203 may be withdrawn to finalize the suturing together of the passages 311 and 351. Using the apparatus 200 of FIG. 2, the coupling segments 201 and 203 may be detached from each other to further facilitate their removal, as shown in the example of FIGS. 7A through 8B.

Figure 7A:
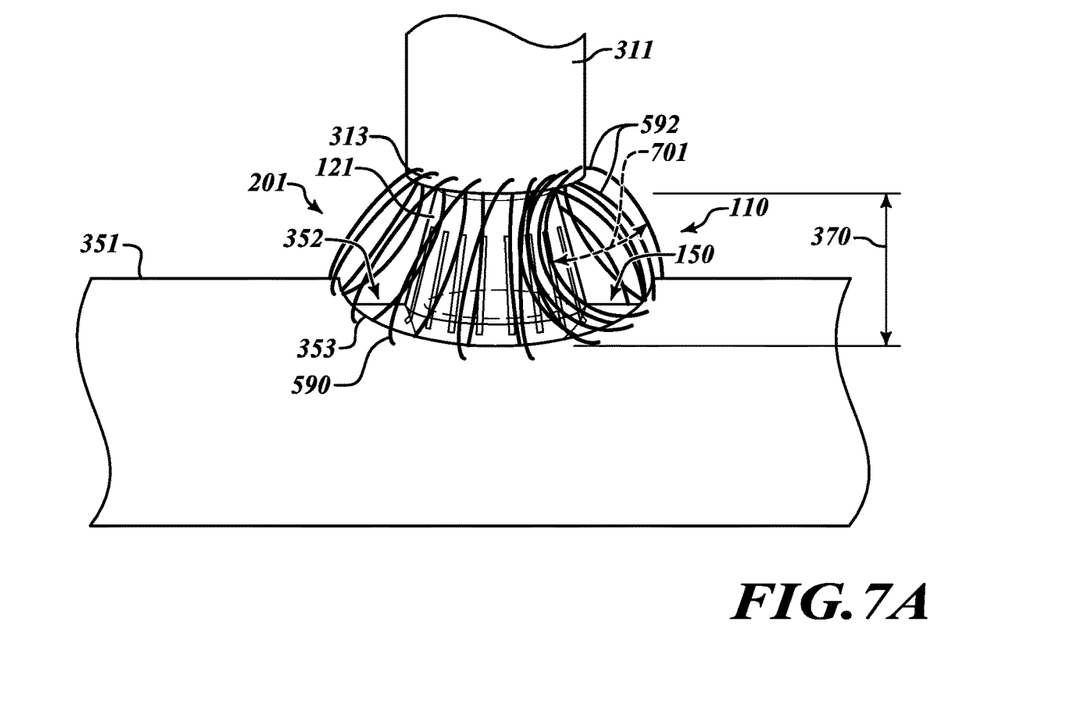
FIGS. 7A-7C are schematic diagrams of removal of the first coupling segment of the apparatus of FIG. 2 from an operational site.
Figure 7B:
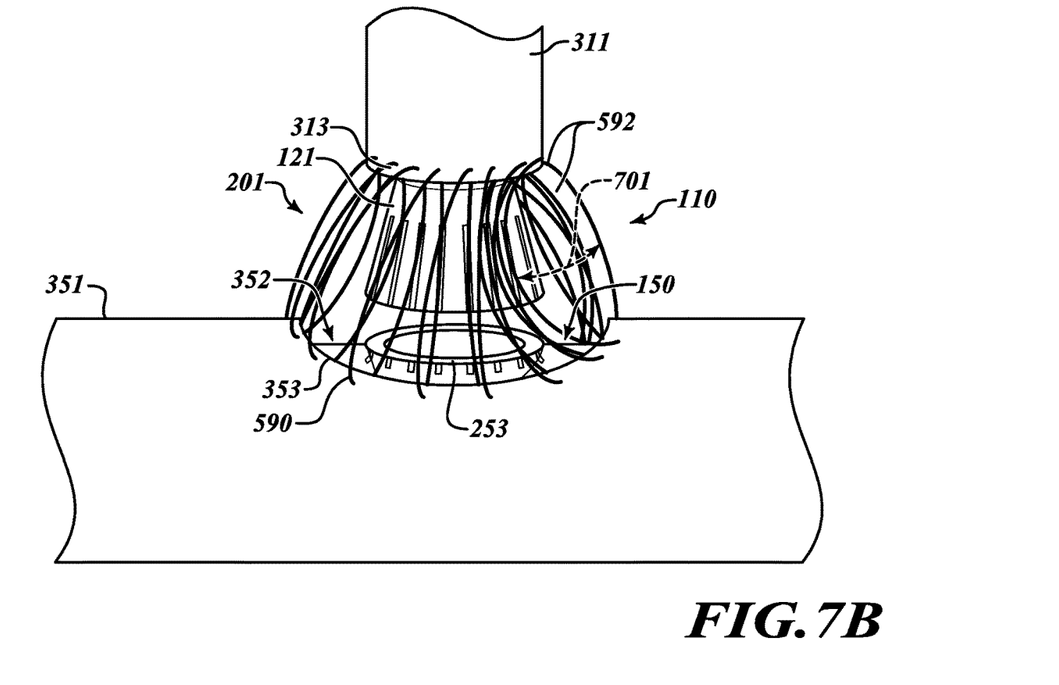
Figure 7C:
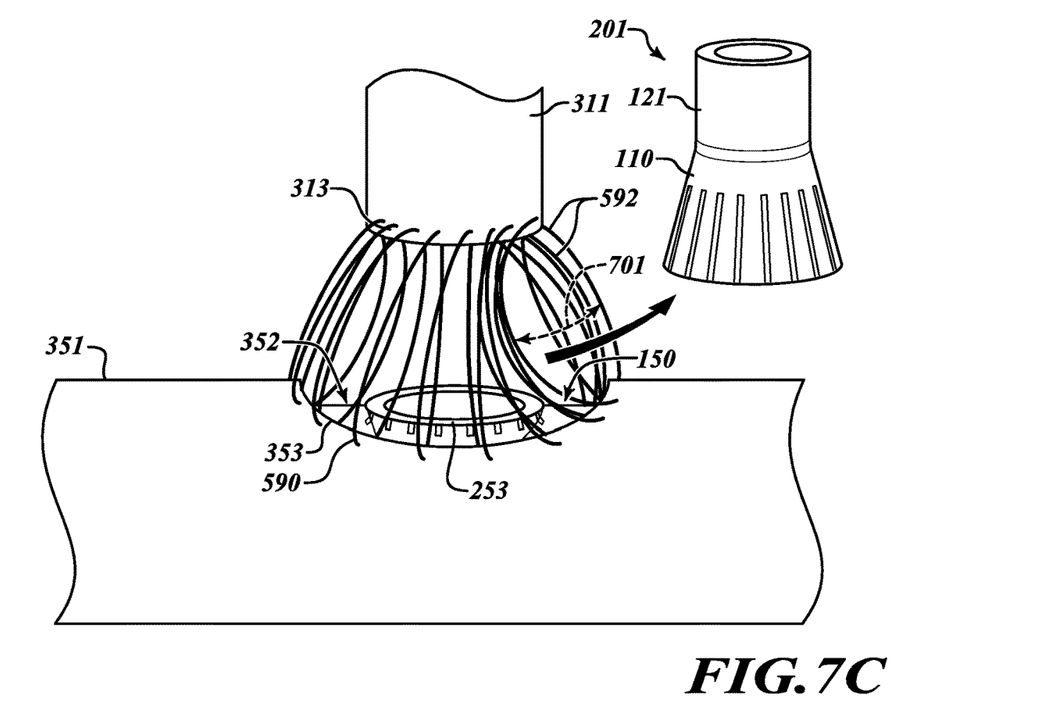

Referring to FIG. 7A, in various embodiments the parachute stitches 592 are separated by an implement or other object (not shown) to form a part 701 between adjacent parachute stitches 592. The part 701 permits access to and removal of the coupling segments 201 and 203. Referring to FIG. 7B, the first connector 110 is removed from the end 313 of the donor passage 311. The base end 220 of the first coupling segment 201 also is detached from the base end 253 of the second coupling segment 203. Referring to FIG. 7C, with the first connector 110 removed from the end 313 of the donor passage 311 and the base end 220 detached, the first coupling segment 201 is then withdrawn through the part 701 between the parachute stiches 592. The first coupling segment 201 may then be removed entirely from the body or other operational site.

It may be desirable to form the part 701 along the edge 353 of the opening 352 adjacent the first end 162 or the second end 164 of the second coupling segment 203. The second coupling segment 203 presents a smaller cross-section at the first end 162 or the second end 164 than along a length of the second coupling segment 203. Thus, when the part 701 is formed adjacent the first end 162 or the second end 164 of the second coupling segment 203, a smaller part 701 may be needed to remove the second coupling segment 203 as compared to the part 701 that may be needed to remove the second coupling segment 203 at a side between the first end 162 and the second end 164. Also, as described with reference to FIGS. 12 and 13, where a first connector 1210 is angled toward the first end 162 of the second connector 203, it may be particularly desirable to form the part 701 adjacent the second end 164 of the second coupling segment 203. In that case, forming the part 701 adjacent the second end 164 of the second coupling segment 203 allows an end 1223 of the first coupling segment 1210 angled away from the part 701 to be drawn through the part 701 to avoid a swept-forward end 1223 from possibly catching on the parachute stiches 592 adjacent the part 701.

Figure 8A:
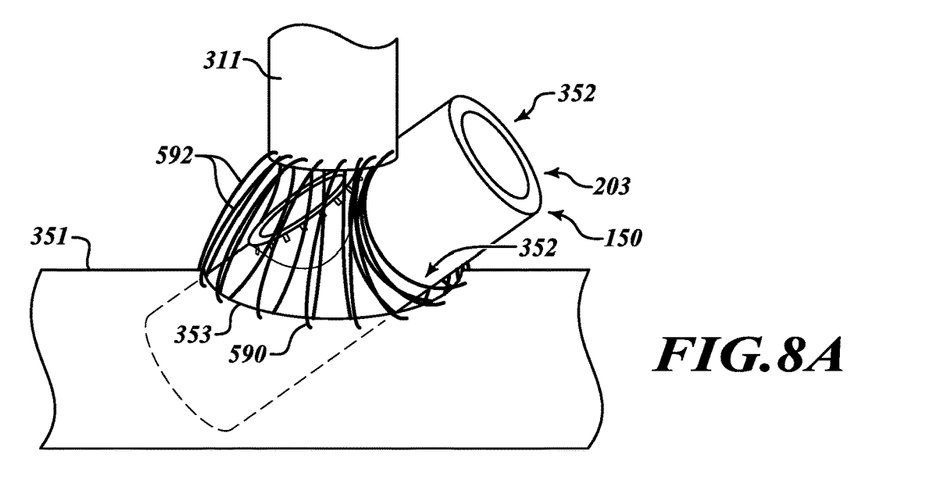
FIGS. 8A and 8B are schematic diagrams of removal of the second coupling segment of the apparatus of FIG. 2 from the operational site.
Figure 8B:
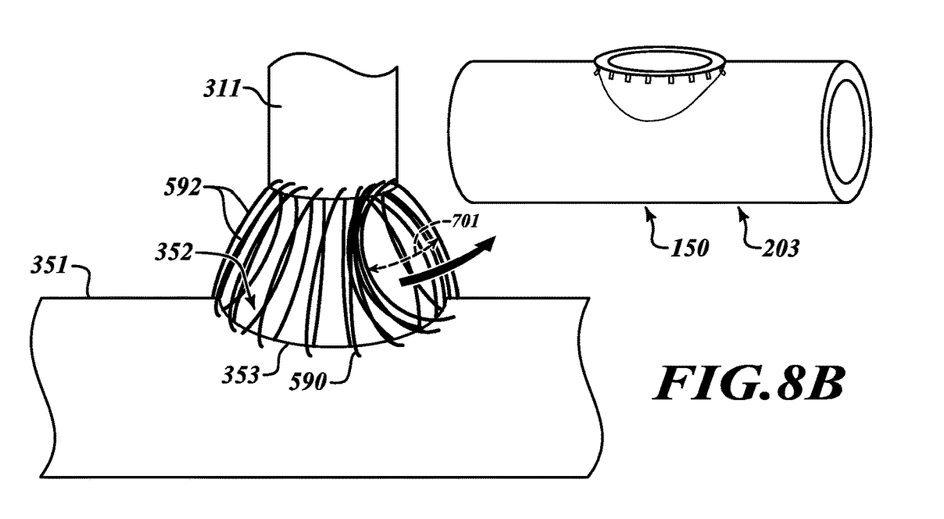

Referring to FIG. 8A, in various embodiments the second coupling segment 203 is accessed through the part 701 in the parachute stiches 592 and removed from the opening 352 in the receiving passage 351. It should be appreciated that prior removal of the first coupling segment 201 as described with reference to FIGS. 7A-7C affords additional room between the parachute stitches 592 in which to engage and remove the second coupling segment 203 from the receiving passage 351. Referring to FIG. 8B, the second coupling segment 203 is withdrawn through the part 701 between the parachute stitches 592. The second coupling segment 203 may then be removed entirely from the body or other operational site.

It will be appreciated that a similar procedure could be performed with an apparatus that does not include separate coupling segments 201 and 203 as shown in FIG. 1. When the parachute stitches 592 are formed loosely enough to allow for a sufficiently large part 701 to be performed, an apparatus without detachable segments may be disconnected from the donor passage 311 and the receiving passage 251 and removed from between the parachute stitches 592.

Figure 9:
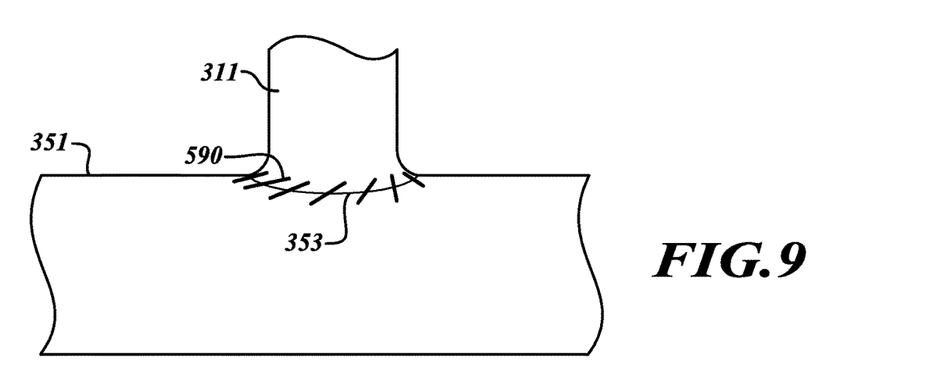
FIG. 9 is a schematic diagram of the tightening of the sutures after removal of the coupling segments of the apparatus of FIG. 2.

Referring to FIG. 9, once the coupling segments 201 and 203 are removed (or an apparatus supporting the connectors 110 and 150 is removed as a single unit), in various embodiments the procedure may be completed by pulling on a loose end 901 of the filament 590 to tighten the parachute stitches 592. It will be appreciated that tightening the parachute stitches 592 draws the end 313 of the donor passage 311 to the edges 353 of the opening 352 in the receiving passage 351, thereby suturing the end 313 of the donor passage 311 to the edges 353 of the opening 352 in the receiving passage 351. With the sutures tightened in place, the loose end 901 of the filament 590 may be tied off, completing the procedure.

Additional embodiments may allow the segments of the apparatus to be separated into smaller components to facilitate their withdrawal after the parachute stitches 592 (FIG. 5B) are formed. Allowing for the segments to be separated into smaller components would allow removal of the components through a smaller part 701 between the parachute stitches 592 and, thus, may allow for the parachute stiches 592 to be shorter or to be formed less loosely. Forming the parachute stitches 592 then may require less tightening of the filament 590 to secure the sutures as described with reference to FIG. 9.

Figure 10A:
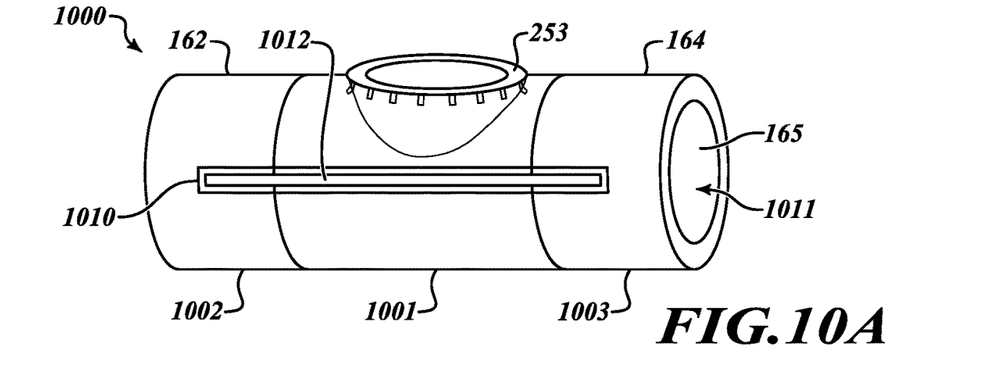
FIGS. 10A and 10B are perspective views of an embodiment of a detachable coupling segment.
Figure 10B:
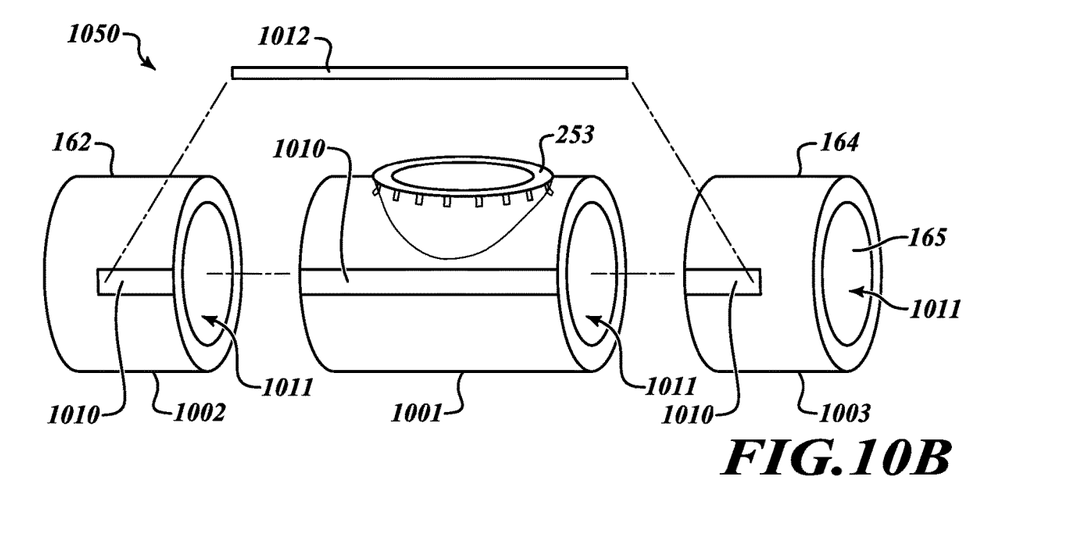

Referring to FIGS. 10A and 10B, for example, a detachable second coupling segment 1000 may include three detachable sections 1001-1003. Referring to FIG. 10A, a first section 1001 may include a main portion of the body 152 and include the base port 253. A second section 1002 may include a first end 162. A third section 1003 may include the second end 164. The sections 1001-1003 may be mated at tongue-and-groove joints (not shown) or be joined in another configuration that would support fluid connections between the base port 253 and/or between the ends 162 and 164 of the second connector 150. The sections 1001-1003 may be held together by one or more support members 1012. The support member 1012 may be a rigid member that engages couplings on an outside of each of the sections 1001-1003 to hold the sections 1001-1003 together. The support member 1010 may also include a wire or other flexible member that frictionally engages a groove 1010 extending across each of the sections 1001-1003 to hold the sections 1001-1003 together.

Referring to FIG. 10B, when the detachable coupling segment 1000 is ready for removal, the support member 1012 may be withdrawn from the groove 1010 across each of the sections 1001-1003 to detach the sections 1001-1003. The support member 1012 may be accessed through the part 701 between the parachute stitches 592 (FIGS. 7A-8B) with a suitable tool or implement (not shown) and removed from the sections 1001-1003. Then, each of the sections 1001-1003 may be separately removed through the part 701 between the parachute stitches 592.

It will be appreciated that, because the individual sections 1001-1003 are smaller than the entirety of second coupling segment 1000, the sections 1001-1003 may be removed through a smaller part 701 between the parachute stitches. Therefore, the parachute stitches 592 may be formed less loosely than if the second coupling segment 1000 were to be removed as a whole. Also, even without the parachute stitches 592 being formed less loosely, the relatively smaller size of the sections 1001-1003 would be easier to remove from between the parachute stitches than removing the second coupling segment 1000 as a whole. It will also be appreciated that the first coupling segment 201 (FIG. 2) similarly could be formed of separate, detachable sections to facilitate their removal from between parachute stitches 592 and from the operative site.

Figure 11:
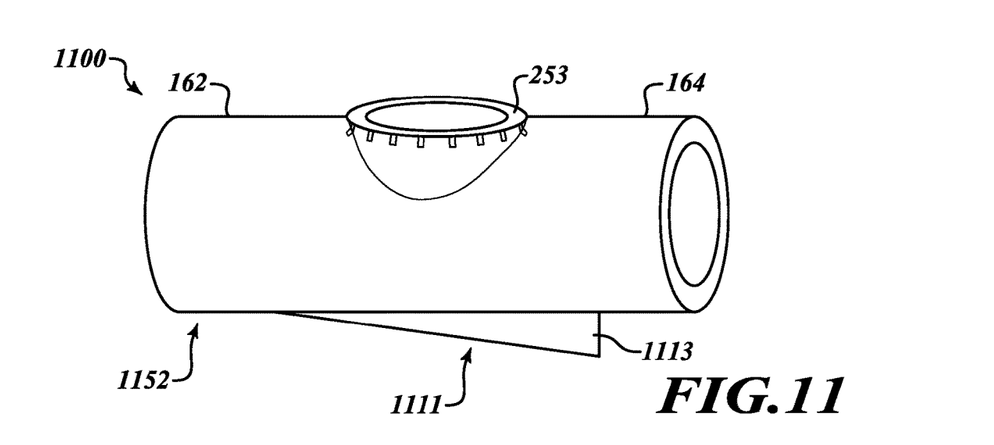
FIG. 11 is a perspective view of an embodiment of a coupling member including an integrated cutting device.

Referring to FIG. 11, a second connector 1150, whether part of a second coupling segment 1100 or part of a unified assembly (not shown), may also include an integrated cutting device 1111. The integrated cutting device 1111 may be used to form the opening 352 in the receiving passage 351 (FIGS. 3A-9) into which the second connector 1150 will be inserted. The integrated cutting device 1111 may include a cutting edge 1113 mounted on an underside 1152 of the second connector 1100. Inclusion of the integrated cutting device 1111 on the underside 1152 of the second connector 1100 may simplify the formation of the opening 352 (FIGS. 3A and 3B) by using the second connector 1100 to perform a cutting step rather than having to insert and to control a separate device, such as an endoscopic scalpel, at the operational site. Instead, the second connector 1100, which already will have to be positioned and controlled at the operational site, could be manipulated to cut the opening 352 prior to its insertion therein.

Figure 12:
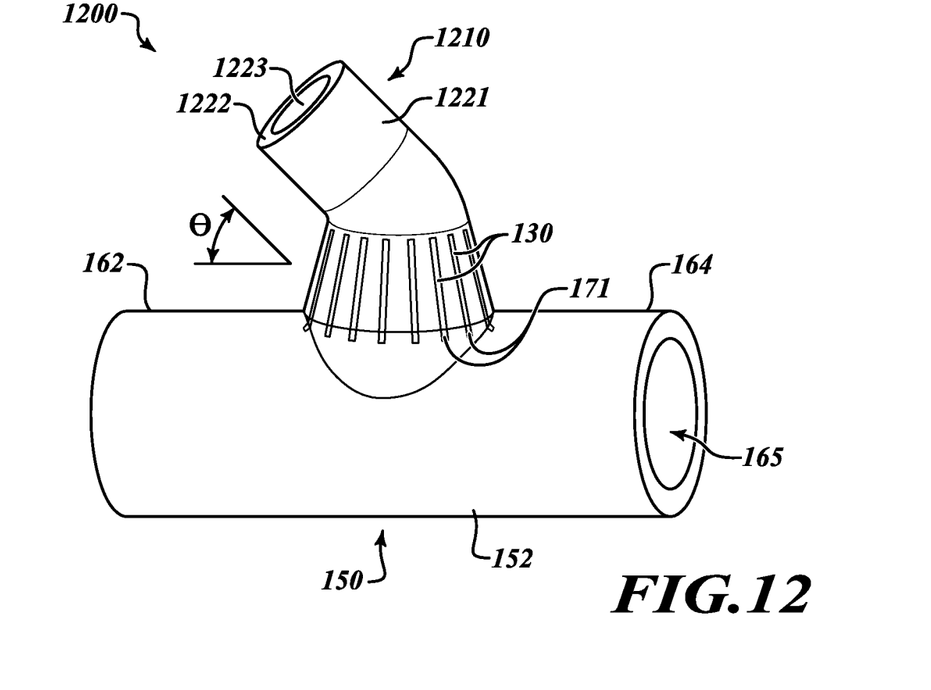
FIG. 12 is a perspective view of an embodiment of an apparatus for temporarily securing passages to be joined in an anastomosis procedure where a donor passage is to be held in place and sutured to the receiving passage at an oblique angle.

Referring to FIG. 12, an apparatus 1200 for facilitating surgical anastomosis of bodily passages is similar to the embodiment of the apparatus 100 of FIG. 1, but where a first connector 1210 is configured to engage the second connector 150 at an oblique angle θ. As with the first connector 110 of the apparatus 100 of FIG. 1, the first connector 1210 is configured to engage a donor passage (not shown in FIG. 12). An end 1222 of the first connector 1210 includes a first port 1223 configured to receive a flow of fluid from the donor passage.

Figure 13:
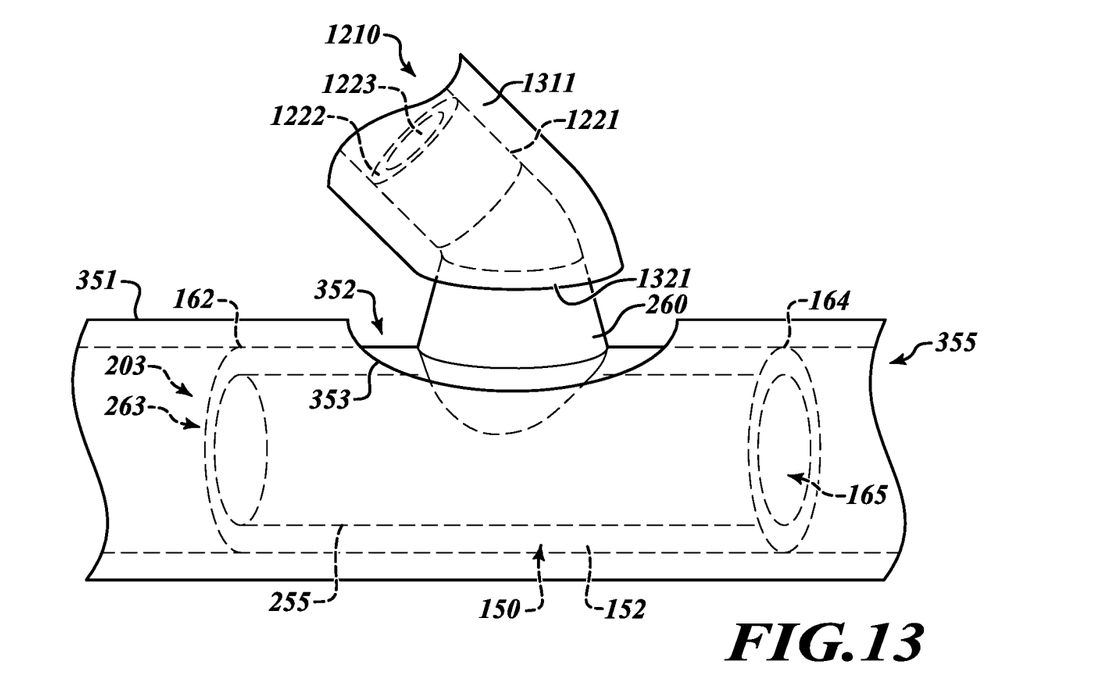
FIG. 13 is a schematic diagram in partial cutaway form of the apparatus of FIG. 12 inserted to temporarily secure the passages.

Referring to FIG. 13, the first connector 1210 engages an angled donor passage 1321 having an angled end 1321 shaped to engage edges 353 of the opening 352 formed in the receiving passage 351. As with the first connector 110 of the apparatus 100 of FIG. 1, the connector 1210 holds the donor passage 1321 in place relative to the receiving passage 351 while they are sutured as described with reference to FIGS. 5A-9.

Figure 14:
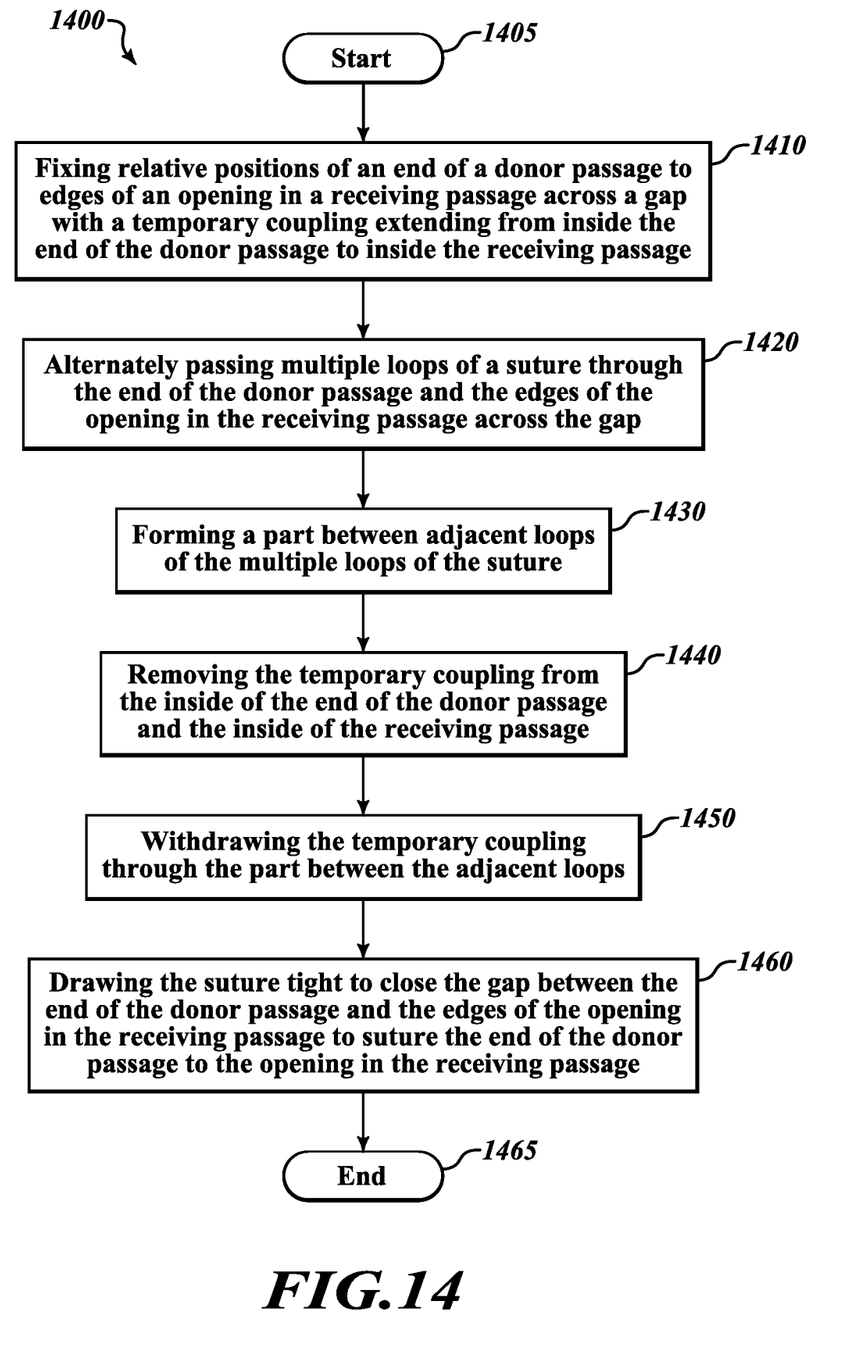
FIG. 14 is a flow diagram of an illustrative method of performing an anastomosis procedure.

Referring to FIG. 14, in various embodiments an illustrative method 1400 of performing an anastomosis procedure is provided. The method 1400 starts at a block 1405. At a block 1410, the position of an end of a donor passage is fixed across a gap relative to edges of an opening in a receiving passage with a temporary coupling extending from inside an end of the donor passage to inside the receiving passage. At a block 1420, multiple loops of a suture are alternately passed through the end of the donor passage and the edges of the opening in the receiving passage across the gap. At a block 1430, a part is formed between adjacent loops of the multiple loops of the suture. At a block 1440, the temporary coupling is removed from the inside of the end of the donor passage and the inside of the receiving passage. At a block 1450, the temporary coupling is withdrawn through the part between the adjacent loops. At a block 1460, the suture is drawn tight to close the gap between the end of the donor passage and the edges of the opening in the receiving passage to suture the end of the donor passage to the opening in the receiving passage. The method 1400 ends at a block 1465, with the end of the donor passage sutured to edges of the opening in the receiving passage to complete the grafting of the donor passage and the receiving passage.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
   a first connector configured to engage an end of a donor passage;
   a second connector configured to engage an opening in a receiving passage; and
   a separator configured to support the first connector and the second connector and further configured to fix relative positions of an opening of the donor passage and edges of the opening in the receiving passage across a gap, wherein the separator is configured to maintain the gap between the first connector and the second connector with multiple loops of a suture being passed through the opening of the donor passage and the edges of the opening in the receiving passage across the gap,
   wherein the first connector, the second connector, and the separator are further configured to be removed from between adjacent loops of the multiple loops of the suture.

2. The apparatus of claim 1, wherein:
   a first coupling segment includes the first connector and the separator, wherein the first connector is configured to be inserted into an opening of the donor passage; and
   a second coupling segment includes the second connector, wherein the second connector is configured to be inserted into the opening in the receiving passage, wherein the first coupling segment and the second coupling segment are configured to be coupled together.

3. The apparatus of claim 2, wherein at least one of:
   the first coupling segment is configured to fluidly connect the donor passage to a second side of the receiving passage to enable a first fluid flow in the donor passage to flow to the second side of the receiving passage; and
   the second coupling segment is configured to fluidly connect a first longitudinal side of the receiving passage to a second longitudinal side of the receiving passage to enable a second fluid flow in the first side of the receiving passage to flow to the second side of the receiving passage.

4. The apparatus of claim 3, wherein the first coupling segment is configured to block the first fluid flow from passing out of the donor passage until the first coupling segment is fluidly connected to the receiving passage.

5. The apparatus of claim 2, wherein at least one of the first coupling segment and the second coupling segment is divisible into one or more sections.

6. The apparatus of claim 1, further comprising a cutting edge disposed adjacent the second connector and configured to cut the opening in the receiving passage.

7. The apparatus of claim 1, further comprising a partial guide channel configured to direct a needle couplable with the suture through the edges of the donor passage and the edges of the opening in the receiving passage across the gap.

8. The apparatus of claim 1, wherein the first connector is configured to present the opening of the donor passage at one of a right angle and at an oblique angle relative to the opening in a receiving passage.

9. A system comprising:

a needle configured to draw a suture through edges of a donor passage and edges of an opening in a receiving passage;

a first connector configured to engage an inside of an end of an opening of the donor passage;

a second connector configured to engage the opening in the receiving passage; and a separator configured to support the first connector and the second connector and further configured to fix relative positions of the opening of the donor passage and the edges of the opening in the receiving passage across a gap, wherein the separator is configured to maintain the gap between the first connector and the second connector with multiple loops of a suture being passed through the edges of the donor passage and the edges of the opening in the receiving passage across the gap, the first connector, the second connector, and the separator being further configured to be removed from between adjacent loops of the multiple loops of the suture.

10. The system of claim 9, wherein:

a first coupling segment includes the first connector, wherein the first connector is configured to be inserted into an opening of the donor passage; and a second coupling segment includes the second connector and the separator, wherein the second connector is configured to be inserted into the opening in the receiving passage, wherein the first coupling segment and the second coupling segment are configured to be coupled together.

11. The apparatus of claim 10, wherein at least one of:

the first coupling segment is configured to fluidly connect the donor passage to a second side of the receiving passage to enable a first fluid flow in the donor passage to flow to the second side of the receiving passage; and the second coupling segment is configured to fluidly connect a first side of the receiving passage to a second longitudinal side of the receiving passage to enable a second fluid flow in the first side of the receiving passage to flow to the second side of the receiving passage.

12. The system of claim 11, wherein the first coupling segment is configured to block the first fluid flow from passing out of the donor passage until the first coupling segment is fluidly connected to the receiving passage.

13. The system of claim 10, wherein at least one of the first coupling segment and the second coupling segment is divisible into one or more sections.

14. The system of claim 9, further comprising a cutting edge disposed adjacent the second connector and configured to cut the opening in the receiving passage.

15. The system of claim 9, further comprising a partial guide channel configured to direct a needle couplable with the suture through the edges of the donor passage and the edges of the opening in the receiving passage across the gap.

16. The system of claim 9, wherein the needle includes one of:

a rigid curved needle; and a flexible needle.

17. The apparatus of claim 9, wherein the first connector is configured to present the opening of the donor passage at one of a right angle and at an oblique angle relative to the opening in a receiving passage.

* * * * *